(12) United States Patent
Soher et al.

(10) Patent No.: US 8,478,380 B2
(45) Date of Patent: Jul. 2, 2013

(54) MAGNETIC RESONANCE THERMOMETRY IN THE PRESENCE OF WATER AND FAT

(75) Inventors: Brian J. Soher, Chapel Hill, NC (US); Scott B. Reeder, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 567 days.

(21) Appl. No.: 12/598,086

(22) PCT Filed: May 1, 2008

(86) PCT No.: PCT/US2008/062139
§ 371 (c)(1),
(2), (4) Date: Feb. 2, 2010

(87) PCT Pub. No.: WO2008/137495
PCT Pub. Date: Nov. 13, 2008

(65) Prior Publication Data
US 2010/0185081 A1 Jul. 22, 2010

Related U.S. Application Data

(60) Provisional application No. 60/927,789, filed on May 4, 2007.

(51) Int. Cl.
*A61B 5/00* (2006.01)

(52) U.S. Cl.
USPC ............ 600/412; 600/407; 600/410; 600/420

(58) Field of Classification Search
USPC ................... 600/410, 412, 420; 324/307–309
See application file for complete search history.

(56) References Cited

U.S. PATENT DOCUMENTS

| 4,914,608 | A | 4/1990 | LeBihan et al. |
| 5,711,300 | A * | 1/1998 | Schneider et al. ............ 600/412 |
| 6,194,899 | B1 | 2/2001 | Ishihara et al. |
| 6,618,608 | B1 | 9/2003 | Watkins et al. |
| 6,856,134 | B1 | 2/2005 | Reeder et al. |
| 8,024,025 | B2 * | 9/2011 | Mallozzi et al. ............ 600/412 |
| 2008/0287773 | A1 * | 11/2008 | Harvey et al. ................ 600/412 |
| 2011/0268332 | A1 * | 11/2011 | Hofstetter et al. ............ 382/131 |
| 2012/0071746 | A1 * | 3/2012 | Vortman et al. ............... 600/411 |

OTHER PUBLICATIONS

CM Gerdes, R Kijowski, SB Reeder. IDEAL Imaging of the Musculoskeletal System: Robust Water-Fat Separation for Uniform Fat Suppression, Marrow Evaluation, and Cartilage Imaging. American Journal of Roentgenology 2007; 189: 284-291.*

SB Reeder, CA McKenzie, AR Pineda, H Yu, A Shimakawa, AC Brau, BA Hargreaves, GE Gold, JH Brittain. Water-Fat Separation with IDEAL Gradient-Echo Imaging. J. Magn. Reson. Imaging 2007; 25: 644-652.*

(Continued)

*Primary Examiner* — Unsu Jung
*Assistant Examiner* — Amanda Lauritzen
(74) *Attorney, Agent, or Firm* — Quarles & Brady, LLP

(57) ABSTRACT

The in vivo measurement of tissue temperature is performed during a medical procedure using an MRI system. Fat and Water images are acquired at each temperature measurement time and corresponding phase images are produced. A temperature map is produced by subtracting the phase at each Fat image pixel from the corresponding pixel in the Water phase image to improve measurement accuracy in tissues with fat/water mixtures.

8 Claims, 3 Drawing Sheets

OTHER PUBLICATIONS

SB Reeder, AR Pineda, A Wen, A Shimakawa, H Yu, JH Brittain, GE Gold, CH Beaulieu, NJ Pelc. Iterative Decomposition of Water and Fat with Echo Asymmetry and Least-Squares Estimation (IDEAL): Application with Fast Spin-Echo Imaging. Magn. Reson. in Med. 2005; 54: 636-644.*

Cousins, J.P. et al: Improved Background Suppression for Intracranial 3D TOF MRA using Robust Fat Suppression with IDEAL at 3T, The Joint Annual Meeting ISMRM-ESMRMB, Book of Abstracts, May 2007, p. 583.

Soher, B.J., et al: Temperature Mapping with IDEAL Water-Fat Phase Differences, The International Society of Magnetic Resonance in Medicine 16th Meeting, Book of Abstracts, May 2008, p. 3018.

International Search Report and Written Opinion Corresponding to PCT/US08/062139 under date of mailing of Aug. 19, 2008.

Cramer-Rao Bounds for Three-Point Decomposition of Water and Fat; Pineda et al.; Magnetic Resonance in Medicine, 54:625-635 (2005).

Temperature Mapping with IDEAL Water-Fat Phase Differences, B.J. Soher, et al.

Multiecho Reconstruction for Simultaneous Water-Fat Decomposition and T2* Estimatation; Huanzhou Yu, et al.; Journal of Magnetic Resonance Imagine 26:1153-1162 (2007).

Improved Background Suppression for Intracranial 3D TOF MRA using Robus Fat Suppression with IDEAL at 3T, J.P. Cousins, et al.

PRF Thermometry Using Iterative Decomposition of Water and Fat, C. Li, et al.; Proc. Intl. Soc. Mag. Reson. Med. 15 (2007).

* cited by examiner

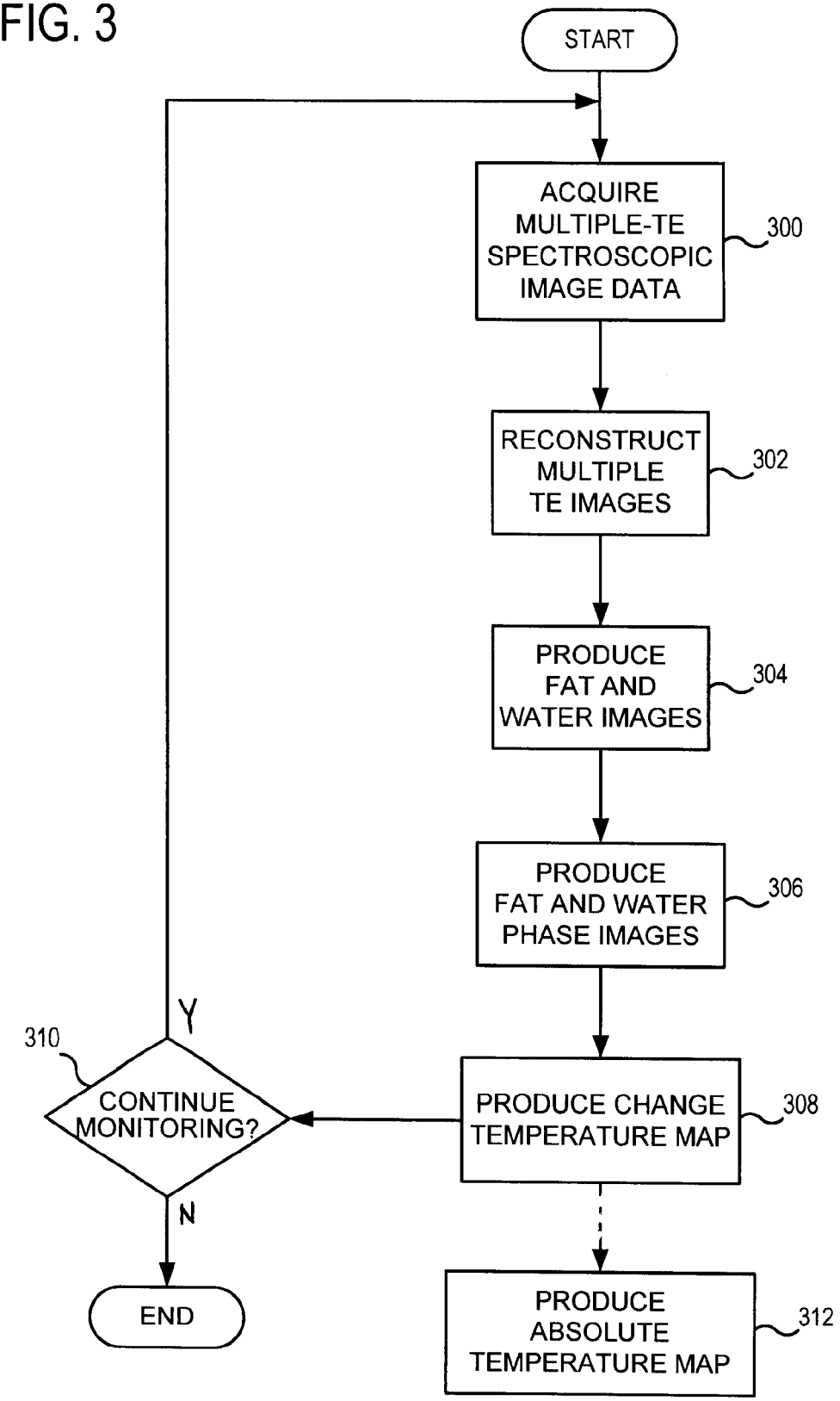

MAGNETIC RESONANCE THERMOMETRY IN THE PRESENCE OF WATER AND FAT

CROSS REFERENCE TO RELATED APPLICATIONS

This application represents the national stage entry of PCT Application No. PCT/US2008/62139 filed on May 1, 2008, and claims the benefit of U.S. Provisional Patent Application 60/927,789 filed 4 May 2007, which is incorporated herein by reference in its entirety for all purposes.

BACKGROUND OF THE INVENTION

The field of the invention is nuclear magnetic resonance imaging methods and systems. More particularly, the invention relates to the in vivo imaging of tissue temperature.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment Mt. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Hyperthermia has been shown to be highly valuable as an adjunct to radiation therapy in such cases as recurrent cancer in the chest wall. One of the key factors in successful hyperthermia treatment is the measurement and control of temperature in the tumor and also in surrounding normal tissue. While invasive thermometry provides accurate and precise measurements, complete temperature mapping of a region using magnetic resonance imaging is expected to afford improvements in the control of the temperature therapy distribution. Non-invasive thermometry is needed for radiofrequency ablation to heat tumors, for cryoablation to freeze tumors and to provide temperature measurements within the tumor as well as the surrounding tissues.

Previous work has shown the value of using the temperature sensitivity of the tissue water proton resonant frequency shift (PUS) or the apparent diffusion coefficient (ADC) to measure temperature change. However, tissues containing a mix of water and lipids, e.g. breast, confound most standard frequency shift thermometry approaches since lipids have no chemical shift dependencies with temperature change.

Recently, a new method known as IDEAL was developed for imaging spin species such as fat and water. As described in U.S. Pat. No. 6,856,134 B1 issued on Feb. 15, 2005 and entitled "Magnetic Resonance Imaging With Fat-Water Signal Separation", the IDEAL method employs pulse sequences to acquire multiple images at different echo times (TE) and an iterative, linear least squares approach to estimate the separate water and fat signal components. The advantage of the IDEAL method is if the frequencies of the particular metabolites being imaged are known, the number of different echo time repetitions can be significantly reduced. This "a priori" information shortens scan time and enables more pulse sequence repetitions to be devoted to increased image resolution.

SUMMARY OF THE INVENTION

The present invention is a method for measuring the temperature of tissues containing a mixture of water and fat using an MRI system. Image data are acquired at three or more echo times ($TE_1$, $TE_2$, $TE_3$) and separate water and fat images are reconstructed. By setting the RF excitation to the Larmor frequency of water, phase shifts caused by temperature can be seen in the phase of fat signals. It has also been discovered that the difference between the water signal phase and the fat signal phase at each image voxel is an indication of the temperature at that location.

A general object of the invention is to non-invasively produce a temperature map of in vivo tissues which contain a mix of tissues containing both lipids and water. A more accurate measure of temperature is achieved by subtracting the phase of a separate lipid/fat image from the phase of a separate water image. The temperature measurement is self-referenced by the phase difference between water and fat signals and phase shifts over the lengthy medical procedure caused by other factors such as $B_0$ field drift do not affect the measurement.

BRIEF DESCRIPTION OF THE DRAWINGS

FIG. 3 is a flow chart of the steps in the preferred embodiment of the invention.

GENERAL DESCRIPTION OF THE INVENTION

Figure 1:
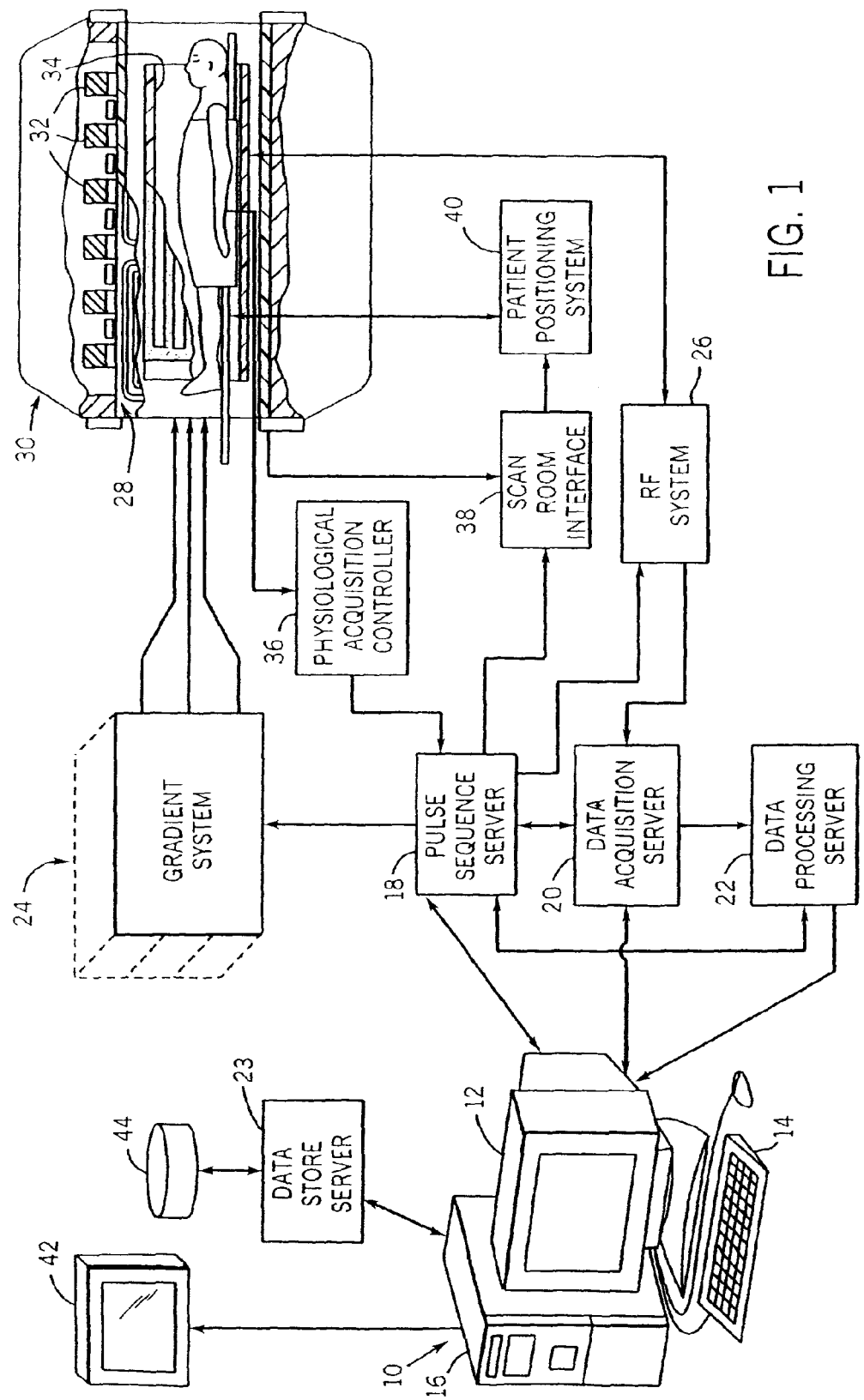
FIG. 1 is a block diagram of an MRI system which employs the present invention.

The standard IDEAL model for water and fat is shown in Eq. 1.

$$S(t_n) = (A_w e^{i\phi_w} + A_f e^{i\phi_f} e^{i\omega_{cs} t_n}) e^{i\psi t_n} \quad (1)$$

If the water frequency changes with temperature this adds a phase change in the water term. However, standard IDEAL post-processing models water as on-resonance, so phase shifts from temperature changes appear in the fat term. This can be written, $$S(t_n) = (A_w e^{i\phi_w} + A_f e^{i\phi_f} e^{i\omega_{cs} t_n} e^{i\omega_{\Delta T} t_n}) e^{i\psi t_n} \quad (2)$$

where $\phi_w$ and $\phi_f$ are constant phase shifts of water and fat. Also note that the chemical shift frequency is the sum of a baseline chemical shift between water and fat ($\omega_o$) at some nominal baseline temperature (e.g., 37° C.) and a temperature dependent frequency, $$\omega_{\Delta T} = \gamma \alpha B_o \Delta T \quad (3)$$

where $\gamma$ is the gyromagnetic ratio ($\gamma/2\pi = 42.58$ MHz/T), $\alpha = -0.01$ ppm/° C. is the PRF change coefficient and $B_0$ is the main magnetic field strength. If the middle of the three echo times, $t_2$, is large compared to the spacing between echoes ($t_2-t_1$ and $t_3-t_2$), then we can ignore the change in phase accumulated during the small time between echoes, ie: assume $t_2-t_1$ and $t_3-t_2$ are small, such that, $$e^{i\omega_{\Delta T} t_n} \approx e^{i\gamma \alpha B_o \Delta T t_2}$$

Therefore, the signal model can now be written $$S(t_n) \approx (A_w e^{i\phi_w} + A_f e^{i\psi_f} e^{i\omega_{cs} t_n} e^{i\gamma \alpha B_o \Delta T t_2}) e^{i\psi t_n} \quad (4)$$

IDEAL water-fat separation is then performed providing complex estimates of water and fat, ie:

$$W = A_w e^{i\phi_w} \quad (5)$$

and $$F = A_f e^{i\psi_f} e^{i\gamma \alpha B_o \Delta T t_2} \quad (6)$$

By measuring the difference in phase between the water and fat at each time point, the temperature can be determined. Specifically, $$\Delta\phi_1 = \phi_w - \phi_f \quad (7)$$

and $$\Delta\phi_2 = \phi_w - \phi_f - \gamma \alpha B_o \Delta T t_2 \quad (8)$$

Temperature change is then estimated as, $$\Delta T = \frac{(\Delta\phi_1 - \Delta\phi_2)}{\gamma \alpha B_o t_2} \quad (9)$$

Alternatively, temperature can be measured from the water signal alone, so long as the resonant frequency of the scanner has not changed between the acquisitions of the reference image and the subsequent images. This is the usual situation and the signal model of the image acquired during heating/cooling can be written, $$S(t_n) = (A_w e^{i\phi_w} e^{i\omega_{cs} t_n} + A_f A_w e^{i\psi_f} e^{i\omega_{cs} t_n}) e^{i\psi t_n} \quad (10)$$

and making the same assumptions as above, $$S(t_n) \approx (A_w e^{i\phi_w} e^{i\gamma \alpha B_o \Delta T t_2} + A_f e^{i\psi_f} e^{i\omega_{cs} t_n}) e^{i\psi t_n} \quad (11)$$

By measuring the phase of the water only image at time 1 ($\phi_{w1}$, reference) and time 2 ($\phi_{w2}$, during heating or cooling), the temperature change is $$\Delta T = \frac{(\phi_{w1} - \phi_{w2})}{\gamma \alpha B_o t_2} \quad (12)$$

It is also possible to measure the absolute temperature by using phase images to determine the relative frequency between water and fat. In this way, we can determine the absolute temperature in tissues that contain both water and fat, without the need for an external reference.

Absolute temperature can be measured with one data set acquired at one time point, so long as the relative frequency between water and fat is known for a baseline temperature. For example, it is well known that $\omega_{cs} = -210$ Hz at 1.5 T at 37° C. or $-220$ Hz at 21° C. In addition, for pulse sequences such as fast spin-echo (FSE) and spoiled gradient echo (SPGR) imaging, as well as other pulse sequences, the relative constant phase of water ($\omega_w$) and fat ($\phi_f$) are equal at t=0. Therefore, the absolute temperature can be determined from a single time point using the following equation:

$$T_{abs} = \frac{(\phi_f - \phi_w)}{\gamma \alpha B_o t_2} + T_{ref} \quad (13)$$

where $T_{ref}$ is the known reference temperature. This reference temperature is the same temperature at which the relative chemical shift between water and fat ($\omega_{cs}$) was measured (eg. $-210$ Hz at 37° C. or $-220$ Hz at 21° C.).

Complex images of fat acquired with the IDEAL method can be used to model an estimate of MR main field drift throughout a volume regardless of temperature changes, e.g., a map of the phase change in the subcutaneous fat surrounding the leg can be used to fit a smoothly changing estimate of the main $B_0$ field over the whole leg (including muscle that does not contain fat). This method can be used clinically to correct real time temperature maps for errors due to $B_0$ field drift over the course of hyperthermia treatment. This method works better than current methods which are based on external fat references placed outside of the leg since the subcutaneous fat is located much closer to the muscle in which we want to estimate the field change.

DESCRIPTION OF THE PREFERRED EMBODIMENT

Referring particularly to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34. In the preferred embodiment a 3.0 Tesla scanner sold by General Electric under the trademark "SIGNA" is employed.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi = \tan^{-1} Q/I.$$

In the preferred embodiment a dual-tuned, proton-carbon transmit and receive local coil is employed such as that described in U.S. Pat. No. 4,799,016 entitled "Dual Frequency NMR Surface Coil."

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing include Fourier transformation of raw k-space NMR data to produce two or three-dimensional images; the application of filters to a reconstructed image and the reconstruction of the metabolic images according to the present invention.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
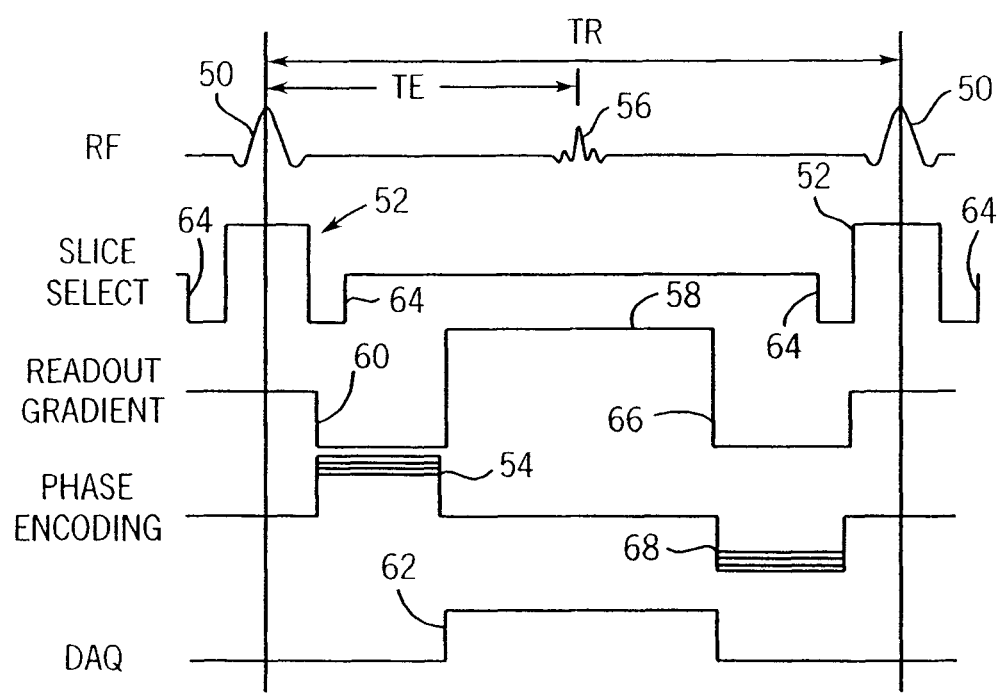
FIG. 2 is a graphic representation of a preferred pulse sequence used to direct the operation of the MRI system of FIG. 1.

A number of different pulse sequences can be used to direct the MRI system to acquire the data needed to practice the present invention. In one preferred embodiment a pulse sequence as shown in FIG. 2 is employed which uses the steady state free precision (SSFP) principle. It includes a selective rf excitation pulse 50 that is repeated at the start of each TR period as well as a slice select gradient pulse 52 that is produced concurrently with the rf pulse 50 to produce transverse magnetization in a prescribed slice. The rf frequency of the pulse 50 is tuned to the Larmor frequency of water spins in the subject being imaged.

After excitation of the spins in the slice a phase encoding gradient pulse 54 is applied to position encode the NMR signal 56 along one direction in the slice. A readout gradient pulse 58 is also applied after a dephasing gradient lobe 60 to position encode the NMR signal 56 along a second, orthogonal direction in the slice. The NMR signal 56 is sampled during a data acquisition window 62. To maintain the steady state condition, the integrals of the three gradients each sum to zero. To accomplish this rephrasing lobes 64 are added to the slice select gradient waveform, a rephrasing lobe 66 is added to the readout gradient waveform and a rewinder gradient lobe 68 is added to the phase encoding gradient waveform. As is well known in the art, the pulse sequence is repeated and the amplitude of the phase encoding gradient 54 and its equal, but opposite rewinder 68 are stepped through a set of values to sample 2D k-space in a prescribed manner.

Referring particularly to FIG. 3, a scan is conducted using this pulse sequence to direct the above MRI system to acquire spectroscopic image data as indicated at process block 300. Three images at three different echo times TE are acquired at each prescribed slice location. Three gradient echo image k-space data sets are thus acquired at each time point with TR=100 ms, FOV=180 mm, 128×128 sample pts, one coronal slice 5 mm thick, 310 Hz/pt and TE=[3.38, 4.17, 4.97].

As indicated at process block 302, the next step is to reconstruct each 2D slice image from each of the three TE k-space data sets. This is accomplished with a conventional complex, 2DFT transformation of each k-space data set. As indicated at process block 304, the next step is to produce separate Fat and Water images from the three reconstructed images. The IDEAL method described in the above-cited U.S. Pat. No. 6,856,131 is employed to accomplish this step and its teachings are incorporated herein by reference.

The resulting Fat and Water images are complex values from which both signal magnitude and phase can be computed at each image voxel as described above. As indicated at process block 306 both a Fat phase image is produced and a Water phase image is produced. A temperature change map is then produced as indicated at process block 308 by subtracting the phase of each Fat phase image from the phase of the corresponding voxel in the Water phase image and calculating the temperature change therefrom between two time points in the procedure as indicated above in equations (7) through (9).

This temperature map may be displayed for use by a physician or the like during a medical procedure, and if temperature monitoring is to continue as determined at decision block 310, the system loops back to acquire further data and repeat the processing thereof. In addition, an absolute temperature map may be produced as indicated at process block 312. Such a temperature map is produced by calculating the absolute temperature at each image voxel using equation (13) described above.

Variations are possible from the preferred embodiment described above. Increased phase differential between time points can be achieved by lengthening the echo times (TE) during data acquisition. The normal voxel size in the preferred embodiment is 1.4×1.4×5 mm, but spatial resolution can be traded off to gain higher SNR. Total acquisition time for each time point is approximately 40 seconds, and up to 12 slices can be acquired in an interleaved manner during this acquisition time.

Water-fat separation methods that measure temperature dependent on phase shifts using fat as an internal phase reference show great promise as a new approach for MR thermometry in fatty tissues such as the breast. While the IDEAL water-fat separation method described in U.S. Pat. No. 6,856,134 is the preferred embodiment, other water-fat separation methods such as those disclosed in U.S. Pat. Nos. 5,225,781; 6,016,057 and 6,091,243 can also be used.

The invention claimed is:

1. A method for measuring the temperature of tissues containing a mixture of water and fat with a magnetic resonance imaging (MRI) system, the steps comprising:
   a) acquiring three image data sets by directing the MRI system to perform a pulse sequence that includes sampling three different echo signals during each repetition of the pulse sequence, each echo signal being formed at a different echo time;
   b) reconstructing a fat phase image from the acquired image data sets;
   c) reconstructing a water phase image from the acquired image data sets; and
   d) producing a temperature map which indicates the tissue temperature at each image voxel using the difference in phase between the water phase image and the fat phase image at the corresponding voxel.

2. The method as recited in claim 1 in which steps a) through d) are repeated during the performance of a medical procedure and a succession of temperature maps are produced to monitor tissue temperature during the procedure.

3. The method as recited in claim 1 in which step d) is performed by calculating a temperature change $\Delta T$ at each image voxel according to the formula:

$$\Delta T = (\Delta \phi_1 - \Delta \phi_2)/\gamma \alpha B_o TE_2$$

where:
   $\Delta \phi_1 = \phi_w - \phi_f$ is the phase difference between water and fat at one time point;
   $\Delta \phi_2 = \phi_w - \phi_f$ is the phase difference between water and fat at a subsequent time point;
   $\gamma$=gyromagnetic constant;
   $\alpha$=is the proton resonance frequency (PRF) change coefficient; and
   $B_o$=polarizing magnetic field strength.

4. The method as recited in claim 1 in which the absolute temperature is calculated in step d).

5. The method as recited in claim 1 in which steps b) and c) are accomplished using an iterative decomposition of water and fat with echo asymmetry and least-squares estimation (IDEAL) method for producing separate fat and water images.

6. The method as recited in claim 5 in which the IDEAL method produces a complex fat image and a complex water image, and the fat phase image and the water phase image are calculated from the respective complex fat and complex water images.

7. The method as recited in claim 1 in which step a) is performed with a pulse sequence having a radio frequency (rf) excitation pulse tuned to the Larmor frequency of water spins in the tissues.

8. The method as recited in claim 7 in which steps b) and c) are accomplished using an iterative decomposition of water and fat with echo asymmetry and least-squares estimation (IDEAL) method for producing separate fat and water images.

* * * * *